(12) United States Patent
Kim

(10) Patent No.: US 12,318,474 B2
(45) Date of Patent: Jun. 3, 2025

(54) COSMETIC COMPOSITION COMPRISING DEAD LACTIC ACID BACTERIA LACTOBACILLUS PLANTARUM MASS OR CULTURE OF LACTIC ACID BACTERIA FOR PREVENTING OR ALLEVIATING SKIN AGING

(71) Applicant: Dr. JCOS INC., Incheon (KR)

(72) Inventor: Hyojung Kim, Incheon (KR)

( * ) Notice: Subject to any disclaimer, the term of this patent is extended or adjusted under 35 U.S.C. 154(b) by 393 days.

(21) Appl. No.: 17/904,614

(22) PCT Filed: Oct. 25, 2021

(86) PCT No.: PCT/KR2021/015017
§ 371 (c)(1),
(2) Date: Aug. 19, 2022

(87) PCT Pub. No.: WO2022/145663
PCT Pub. Date: Jul. 7, 2022

(65) Prior Publication Data
US 2023/0106788 A1    Apr. 6, 2023

(30) Foreign Application Priority Data
Dec. 30, 2020   (KR) .......................... 10-2020-0188498

(51) Int. Cl.
| | | |
|---|---|---|
| *A61K 8/99* | (2017.01) | |
| *A61Q 19/00* | (2006.01) | |
| *A61Q 19/02* | (2006.01) | |
| *A61Q 19/08* | (2006.01) | |
| *C12N 1/20* | (2006.01) | |
| *C12R 1/25* | (2006.01) | |

(52) U.S. Cl.
CPC .............. *A61K 8/99* (2013.01); *A61Q 19/007* (2013.01); *A61Q 19/02* (2013.01); *A61Q 19/08* (2013.01); *C12N 1/205* (2021.05); *A61K 2800/522* (2013.01); *A61K 2800/782* (2013.01); *C12R 2001/25* (2021.05)

(58) Field of Classification Search
None
See application file for complete search history.

(56) References Cited

FOREIGN PATENT DOCUMENTS

| | | |
|---|---|---|
| KR | 10-2019-0002836 A | 1/2019 |
| KR | 10-2019-0034796 A | 4/2019 |
| KR | 10-2019-0055552 A | 5/2019 |
| KR | 10-2019-0056176 A | 5/2019 |
| KR | 10-2019-0056177 A | 5/2019 |
| KR | 10-2047459 B1 | 11/2019 |

*Primary Examiner* — David J Blanchard
*Assistant Examiner* — Kaeleigh E Olsen
(74) *Attorney, Agent, or Firm* — KORUS Patent, LLC; Seong Il Jeong

(57) ABSTRACT

The present invention relates to a cosmetic composition for preventing or improving aging that comprises a culture of one or more lactic acid bacteria selected from a group consisting of *Lactobacillus plantarum* Wikim 125 (Accession No. KCCM13498P) isolated from Kimchi and *Lactobacillus plantarum* Wikim 126 (Accession No. KCCM13499P) and the *Lactobacillus plantarum* Wikim 127 (Accession No. KCCM13500P) that are isolated from Sauerkraut and may further comprise a dead cell of one or more lactic acid bacteria selected from the group. The cosmetic composition for preventing or improving aging of the present invention can promote skin aging improvement effects through antioxidation, inflammation relief, moisturizing enhancement, skin tone improvement, elasticity and wrinkle improvement, by using natural derived lactic acid bacteria that are skin-friendly, safe, and capable of improving skin functions and cultures using these lactic acid bacteria.

8 Claims, 6 Drawing Sheets

COSMETIC COMPOSITION COMPRISING DEAD LACTIC ACID BACTERIA LACTOBACILLUS PLANTARUM MASS OR CULTURE OF LACTIC ACID BACTERIA FOR PREVENTING OR ALLEVIATING SKIN AGING

FIELD OF THE INVENTION

The present invention relates to a cosmetic composition comprising dead lactic acid bacteria *Lactobacillus plantarum* mass or culture of lactic acid bacteria for preventing or alleviating skin aging.

BACKGROUND OF THE INVENTION

Vegetable lactic acid bacteria are lactic acid bacteria isolated from fermented foods such as pickles and kimchi, and there are a lot of different types compared to animal lactic acid bacteria, and they have excellent adaptability to the external environment. In particular, vegetable lactic acid bacteria isolated from kimchi are known to be excellent in the production of various physiologically active materials because they grow in a barren environment. Accordingly, development of cosmetic materials using lactic acid bacteria isolated from kimchi, their dead cells, and cultures is being actively conducted.

Kimchi is food fermented by lactic acid bacteria, and lactic acid bacteria isolated from kimchi include *Leuconostoc mesenteroides, Leuconostoc dextranicum, Lactobacillus brevis, Lactobacillus plantarum, Pediococcus pentosacues*, and the like.

In the prior arts regarding *Lactobacillus plantarum*, a cosmetic composition for improving skin wrinkles that comprises dead cells of *Lactobacillus plantarum* nF1 strain (Access No. NITE P-1462) isolated from kimchi (Korean Patent Publication No. 2019-0002836), *Lactobacillus plantarum* WiKim0060 (*Lactobacillus plantarum* WiKim0060) isolated from kimchi and a composition for skin lightening and moisturizing that comprises the same (Korean Patent Publication No. 2019-0055552), a cosmetic composition for improving skin wrinkle and a composition for antimicrobial skin protection that comprise cultures of *Lactobacillus plantarum* CJLP133 strain from which cells thereof have been removed. However, these prior patents relate only to one or two effects such as wrinkle improvement in skin aging, lightening improvement, and moisturizing improvement and does not provide an overall improvement effect for skin aging through antioxidation, inflammation relief, moisturizing enhancement, skin tone improvement, and elasticity and wrinkle improvement.

Currently, consumers demand multifunctional cosmetics that comprehensively provide functions for preventing or improving complex aging processes such as an antioxidant effect, an anti-inflammatory effect, moisturizing enhancement, wrinkle improvement, and lightening improvement, in addition to a single function. Accordingly, it is necessary to provide a multi-functional cosmetic that meets the needs of consumers through the development of lactic acid bacteria that are safe for the skin.

DETAILED DESCRIPTION OF THE INVENTION

Technical Problems

An object of the present invention is to provide a cosmetic composition for preventing or improving skin aging that shows skin improvement effects through antioxidation, inflammation relief, moisturizing enhancement, skin tone improvement, elasticity and wrinkle improvement by using natural materials that are skin-friendly, safe, and capable of improving skin functions and that can satisfy desires to look younger.

SUMMARY OF THE INVENTION

The inventor of the present invention has found that cultures and dead cells of *Lactobacillus plantarum* Wikim 125 (Accession No. KCCM13498P) isolated from Kimchi and *Lactobacillus plantarum* Wikim 126 (Accession No. KCCM13499P) and the *Lactobacillus plantarum* Wikim 127 (Accession No. KCCM13500P) that are isolated from Sauerkraut prepared from cabbage are natural materials that are skin-friendly, safe, and capable of improving skin functions and promote prevention and improvement of skin aging through antioxidation, inflammation relief, moisturizing enhancement, skin tone improvement, elasticity and wrinkle improvement and has completed the present invention based on these. *Lactobacillus plantarum* Wikim 125, *Lactobacillus plantarum* Wikim 126, and *Lactobacillus plantarum* Wikim 127 were deposited with the Korean Culture Center of Microorganisms (KCCM), an International Depositary Authority (IDA), located at Yurim B/D, 45, Hongjenae-2ga-gil, Seodaemun-gu, Seoul 03641, Republic of Korea, for the purpose of applying for a Korean patent on Oct. 15, 2020 (date of the original deposits). The accession numbers for the original deposits are KCCM13498P, KCCM13499P, and KCCM13500P, respectively. A request to convert these original deposits to deposits under the Budapest Treaty was made on Jul. 19, 2024, and the accession numbers after conversion are KCCM13498P, KCCM13499P, and KCCM13500P, respectively.

Accordingly, the technical means of the present invention for achieving the objects above are as follows:

1. A cosmetic composition for preventing or improving skin aging that prevents or improves skin aging through antioxidation, anti-inflammation, moisturizing enhancement, wrinkle improvement and skin tone lightening, comprising: a culture of one or more lactic acid bacteria selected from a group consisting of *Lactobacillus plantarum* Wikim 125 (Accession No. KCCM13498P), *Lactobacillus plantarum* Wikim 126 (Accession No. KCCM13499P), and *Lactobacillus plantarum* Wikim 127 (Accession No. KCCM13500P).

2. The cosmetic composition for preventing or improving skin aging of 1, further comprising a dead cell of one or more lactic acid bacteria selected from a group consisting of *Lactobacillus plantarum* Wikim 125 (Accession No. KCCM13498P), *Lactobacillus plantarum* Wikim 126 (Accession No. KCCM13499P), and *Lactobacillus plantarum* Wikim 127 (Accession No. KCCM13500P).

3. The cosmetic composition for preventing or improving skin aging of any one of 1 or 2, wherein the *Lactobacillus plantarum* Wikim 125 (Accession No. KCCM13498P) is isolated from Kimchi.

4. The cosmetic composition for preventing or improving skin aging of any one of claim 1 or 2, wherein the *Lactobacillus plantarum* Wikim 126 (Accession No. KCCM13499P) and the *Lactobacillus plantarum* Wikim 127 (Accession No. KCCM13500P) are isolated from Sauerkraut prepared from cabbage or brussels sprout.

5. The cosmetic composition for preventing or improving skin aging of claim 1, wherein the culture of the lactic acid bacteria is formed by lyophilizing supernatant obtained by culturing the lactic acid bacteria in a lactic acid bacteria culture medium and performing centrifugation.

6. The cosmetic composition for preventing or improving skin aging of claim 1, wherein the dead cells of the lactic acid bacteria are obtained by culturing the lactic acid bacteria in a lactic acid bacteria culture medium, performing centrifugation, and then heat-treating precipitated cells of the lactic acid bacteria.

Technical Effects of the Invention

According to the present invention, a cosmetic composition for preventing or improving aging that comprises a culture of one or more lactic acid bacteria selected from a group consisting of *Lactobacillus plantarum* Wikim 125 (Accession No. KCCM13498P), *Lactobacillus plantarum* Wikim 126 (Accession No. KCCM13499P), and *Lactobacillus plantarum* Wikim 127 (Accession No. KCCM13500P) and may further comprise one or more dead cells of the lactic acid bacteria, is provided.

The present invention can have an effect of promoting prevention and improvement of skin aging to look younger through antioxidation, inflammation relief, moisturizing enhancement, skin tone improvement, elasticity and wrinkle improvement, by using natural derived lactic acid bacteria that are skin friendly, safe, and capable of improving skin functions and cultures using these lactic acid bacteria.

BEST MODE FOR THE INVENTION

Figure 1A:
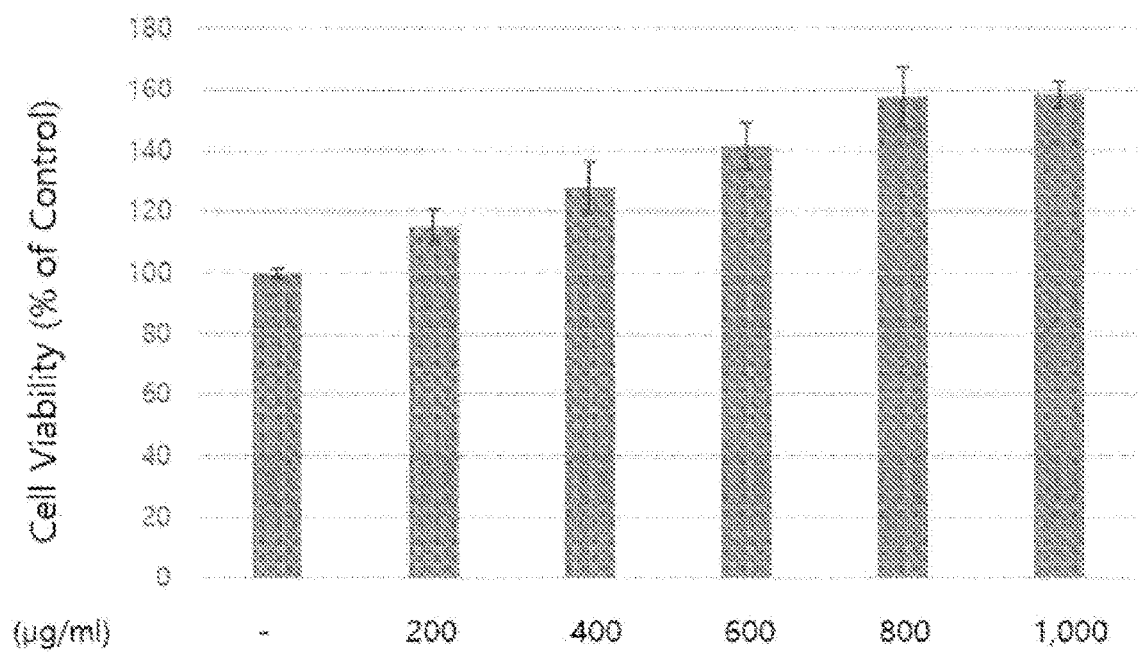
FIG. 1*a* shows a confirmation result of cytotoxicity in Hs68 cells for a composition of Example 7 of the present invention.

The present invention relates to a cosmetic composition for preventing or improving skin aging that comprises cultures of one or more lactic acid bacteria selected from a group consisting of *Lactobacillus plantarum* Wikim 125 (Accession No. KCCM13498P), *Lactobacillus plantarum* Wikim 126 (Accession No. KCCM13499P), and *Lactobacillus plantarum* Wikim 127 (Accession No. KCCM13500P).

Modes for the Invention

In the present invention, the *Lactobacillus plantarum* Wikim 125 (Accession No. KCCM13498P) may be isolated from Kimchi, and the *Lactobacillus plantarum* Wikim 126 (Accession No. KCCM13499P) and the *Lactobacillus plantarum* Wikim 127 (Accession No. KCCM13500P) may be isolated from Sauerkraut, for example, Sauerkraut prepared from cabbage or brussels sprout.

In the present invention, the cultures of the lactic acid bacteria may be formed by lyophilizing supernatant obtained by culturing one or more lactic acid bacteria selected from a group consisting of *Lactobacillus plantarum* Wikim 125 (Accession No. KCCM13498P), *Lactobacillus plantarum* Wikim 126 (Accession No. KCCM13499P), and *Lactobacillus plantarum* Wikim 127 (Accession No. KCCM13500P) in a lactic acid bacteria culture medium such as MRS agar medium and performing centrifugation.

The cosmetic composition for preventing or improving skin aging may further comprise dead cells of one or more lactic acid bacteria selected from a group consisting of *Lactobacillus plantarum* Wikim 125 (Accession No. KCCM13498P), *Lactobacillus plantarum* Wikim 126 (Accession No. KCCM13499P), and *Lactobacillus plantarum* Wikim 127 (Accession No. KCCM13500P)

In the present invention, the dead cells of the lactic acid bacteria may be obtained by a method known in the field of the present invention, for example, by culturing the lactic acid bacteria a lactic acid bacteria culture medium such as MRS agar medium, performing centrifugation, and then heat-treating precipitated cells of the lactic acid bacteria.

The cosmetic composition for preventing or improving skin aging according to the present invention may further comprise additional ingredients commonly used in cosmetic compositions, including at least one component selected from a group consisting of a pH adjuster, surfactant, oil, fat, alcohol, humectant, sterilization preservative, a chelating agent, fragrance, pigment, a UV absorber, a UV scattering agent, and an antioxidant agent, if necessary but is not limited thereto. Specific types and amounts of these additional ingredients are well known in the field of the present invention.

The formulation of the cosmetic composition for preventing or improving skin aging according to the present invention is not limited to a particular form. For example, the formulation of the cosmetic composition of the present invention may be provided in a form of flexible lotion, astringent lotion, nourishing lotion, eye cream, nourishing cream, massage cream, cleansing cream, cleansing foam, cleansing water, powder, ampoule, essence, BB cream, sun cream, a pack, lip balm, or the like. In addition, each formulation of the cosmetic composition for preventing or improving skin aging according to the present invention is not particularly limited thereto and may be selected and mixed by a person skilled in the art without difficulties according to purposes of the compositions.

EXAMPLES

Hereinafter, the present invention will be described in more detail with reference to Examples. However, the following examples are only for illustrating the present invention, and the present invention is not limited to scopes of these examples.

Preparation Example 1: Preparation of Dead Cells of Lactic Acid Bacteria

Dead cells of Lactic acid bacteria were obtained by culturing *Lactobacillus plantarum* Wikim 125 isolated from kimchi (Accession No.: KCCM13498P), *Lactobacillus*

*plantarum* Wikim 126 isolated from sauerkraut prepared from brussels sprouts from Jeju, Korea (Accession No.: KCCM13499P), *Lactobacillus plantarum* Wikim 127 (Accession No.: KCCM13500P) isolated from sauerkraut prepared from cabbage from Jeju, Korea, for 24 hours at 30° C. in MRS agar medium, performing centrifugation, and then heat-treating the precipitated cells at 80° C. for 60 minutes.

[Table 1] Example of production of lactic acid bacteria dead cells

TABLE 1

Example of production of lactic acid bacteria dead cells

| Example | *Lactobacillus* Culture |
|---|---|
| Example 1 (Dead Cell 1) | Dead cells of *Lactobacillus plantarum* Wikim 125 (Accession No.: KCCM13498P) |
| Example 2 (Dead Cell 2) | Dead cells of *Lactobacillus plantarum* Wikim 126 (Accession No.: KCCM13499P), |
| Example 3 (Dead Cell 3) | Dead cells of *Lactobacillus plantarum* Wikim 127 (Accession No.: KCCM13500P) |

Preparation Example 2: Preparation of Cultures of Lactic Acid Bacteria

Cultures of Lactic acid bacteria dead cells were obtained by lyophilizing supernatant obtained by culturing *Lactobacillus plantarum* Wikim 125 isolated from kimchi (Accession No.: KCCM13498P), *Lactobacillus plantarum* Wikim 126 isolated from sauerkraut prepared from brussels sprouts from Jeju, Korea (Accession No.: KCCM13499P). *Lactobacillus plantarum* Wikim 127 (Accession No.: KCCM13500P) isolated from sauerkraut prepared from cabbage from Jeju, Korea, for 24 hours at 30° C. in MRS agar medium and performing centrifugation.

TABLE 2

Example of production of lactic acid bacteria dead cells

| Example | *Lactobacillus* Culture |
|---|---|
| Example 4 (Culture 4) | Cultures of *Lactobacillus plantarum* Wikim 125 (Accession No.: KCCM13498P) |
| Example 5 (Culture 5) | Cultures of *Lactobacillus plantarum* Wikim 126 (Accession No.: KCCM13499P), |
| Example 6 (Culture 6) | Cultures of *Lactobacillus plantarum* Wikim 127 (Accession No.: KCCM13500P) |

Preparation Example 3: Preparation of Mixed Composition of Dead Cells and Cultures of Lactic Acid Bacteria The mixed composition was prepared by mixing the dead cells and the cultures of the lactic acid bacteria prepared in Preparation Examples 1 and 2 in a composition ratio, weight ratio, shown in Table 3 below.

TABLE 3

Composition Ratio of Mixed Compositions

| Composition | Example 7 | Example 8 | Example 9 | Example 10 | Example 11 | Example 12 | Example 13 | Example 14 | Example 15 | Example 16 | Example 17 |
|---|---|---|---|---|---|---|---|---|---|---|---|
| Dead Cell 1 | 20.0 | 25.0 | 50.0 | 20.0 | 40.0 | 25.0 | 75.0 | 67.0 | 50.0 | 60.0 | 0.0 |
| Dead Cell 2 | 60.0 | 70.0 | 25.0 | 20.0 | 20.0 | 75.0 | 0.0 | 0.0 | 0.0 | 0.0 | 33.0 |
| Dead Cell 3 | 10.0 | 5.0 | 25.0 | 40.0 | 60.0 | 0.0 | 25.0 | 33.0 | 50.0 | 40.0 | 67.0 |
| Culture 4 | 4.0 | 0.0 | 0.0 | 0.0 | 0.0 | 0.0 | 0.0 | 0.0 | 0.0 | 0.0 | 0.0 |
| Culture 5 | 50.0 | 0.0 | 0.0 | 0.0 | 0.0 | 0.0 | 0.0 | 0.0 | 0.0 | 0.0 | 0.0 |
| Culture6 | 1.0 | 0.0 | 0.0 | 0.0 | 0.0 | 0.0 | 0.0 | 0.0 | 0.0 | 0.0 | 0.0 |
| Total | 100.0 | 100.0 | 100.0 | 100.0 | 100.0 | 100.0 | 100.0 | 100.0 | 100.0 | 100.0 | 100.0 |

Experimental Example 1: Evaluation of In Vitro Efficacy

In order to verify overall effectiveness of skin aging improvement for each of the lactic acid bacteria dead cells, lactic acid bacteria cultures, and the mixed composition of the lactic acid bacteria dead cells and cultures prepared in Preparation Examples 1 to 3, Antioxidation (active oxygen (ABTS) scavenging ability), anti-inflammation (NO inhibition), anti-inflammation and moisturizing enhancement (hyaluronidase inhibition), lightening (tyrosinase inhibition), and elasticity improvement (collagenase inhibition) were evaluated. In the case of Examples 1 and 2, the evaluation result was excellent in all the evaluation criteria and accordingly, it was confirmed that the compositions are useful for improving skin aging. The experimental procedures and evaluation results are as follows.

Experimental Example 1-1: Evaluation of Antioxidant Effect (Active Oxygen (ABTS) Scavenging Ability)

The ABTS+[2,2'-Azino-bis(3-ethyl benzothiazoline-6-sulfonic acid)] radical scavenging activity, which is part of measurement of an antioxidant activity, can measure both hydrogen-donating antioxidants and chain breaking antioxidants, and it is a measurement method applicable to both aqueous phase and organic phase.

In the present invention, an ABTS radical solution formed by mixing 2.45 mM potassium persulfate in a 7 mM ABTS solution at a ratio of 1:1 (v/v) to be reacted in a dark room for about 24 hours, was mixed with the sample and heated for 10 minutes in a dark room, and then, absorbance was measured at 734 nm. The ABTS radical scavenging ability (%) was calculated using the following formula and shown in [Table 4].

ABTS Radical Scavenging Ability (%)=(Absorbance of Test Group/Absorbance of Untreated Group)×100

TABLE 4

Antioxidant Effect (Active Oxygen (ABTS) Scavenging Ability) Evaluation Result

| Sample | Test Concentration | Active Oxygen (ABTS) Scavenging Ability (%) |
|---|---|---|
| Example 1 | 50 mg/mL | 98.69 |
| Example 2 | 50 mg/mL | 99.42 |
| Example 3 | 50 mg/mL | 97.08 |
| Example 4 | 1 mg/mL | 36.37 |
| Example 5 | 1 mg/mL | 52.02 |
| Example 6 | 1 mg/mL | 41.05 |
| Example 7 | 1 mg/mL | 55.29 |
| Example 8 | 1 mg/mL | 51.00 |
| Example 9 | 1 mg/mL | 42.53 |
| Example 10 | 1 mg/mL | 45.68 |
| Example 12 | 1 mg/mL | 47.81 |
| Example 13 | 1 mg/mL | 39.30 |

In addition, a minimum inhibitory concentration (IC 50, mg/ml) that inhibits the activity of ABTS radicals by 50% was evaluated for Examples 4 to 6 (Cultures 1 to 3). As shown in [Table 5] to [Table 7], the ABTS radical scavenging effect was excellent even at low concentrations of 1.47 mg/ml, 0.96 mg/ml, and 1.35 mg/ml in Examples 4 to 6, respectively.

TABLE 5

Evaluation Result of Antioxidant Effect by Concentration of Culture 1

| Sample | Concentration (mg/mL) | O.D. 734 nm | | | Average | Standard Deviation (%) | Inhibition Rate (%) |
|---|---|---|---|---|---|---|---|
| Untreated Group | — | 0.56 | 0.561 | 0.556 | 0.559 | — | — |
| Example 4 | 0.1 | 0.536 | 0.531 | 0.537 | 0.535 | 0.58 | 4.35 |
| | 0.2 | 0.532 | 0.527 | 0.525 | 0.528 | 0.65 | 5.55 |
| | 0.4 | 0.494 | 0.492 | 0.493 | 0.493 | 0.18 | 11.81 |
| | 0.6 | 0.458 | 0.454 | 0.452 | 0.454 | 0.72 | 18.78 |
| | 1.0 | 0.358 | 0.358 | 0.351 | 0.356 | 0.72 | 36.37 |
| | 2.0 | 0.198 | 0.195 | 0.188 | 0.194 | 0.92 | 65.35 |
| | 5.0 | 0.012 | 0.011 | 0.019 | 0.014 | 0.78 | 97.5 |

TABLE 6

Evaluation Result of Antioxidant Effect by Concentration of Culture 2

| Sample | Concentration (mg/mL) | O.D. 734 nm | | | Average | Standard Deviation (%) | Inhibition Rate (%) |
|---|---|---|---|---|---|---|---|
| Untreated Group | — | 0.608 | 0.609 | 0.611 | 0.609 | — | — |
| Example 5 | 0.1 | 0.575 | 0.578 | 0.577 | 0.577 | 0.25 | 5.36 |
| | 0.2 | 0.561 | 0.554 | 0.555 | 0.557 | 0.62 | 8.64 |
| | 0.4 | 0.505 | 0.513 | 0.502 | 0.507 | 0.93 | 16.85 |
| | 0.6 | 0.459 | 0.455 | 0.451 | 0.455 | 0.66 | 25.33 |
| | 1 | 0.289 | 0.298 | 0.29 | 0.292 | 0.81 | 52.02 |
| | 2 | 0.217 | 0.184 | 0.195 | 0.199 | 2.76 | 67.4 |
| | 5 | 0.002 | 0.003 | 0.004 | 0.003 | 0.34 | 99.62 |

TABLE 7

Evaluation Result of Antioxidant Effect by Concentration of Culture 3

| Sample | Concentration (mg/mL) | O.D. 734 nm | | | Average | Standard Deviation (%) | Inhibition Rate (%) |
|---|---|---|---|---|---|---|---|
| Untreated Group | — | 0.595 | 0.595 | 0.593 | 0.594 | — | — |
| Example 5 | 0.1 | 0.571 | 0.567 | 0.563 | 0.567 | 0.67 | 4.6 |
| | 0.2 | 0.547 | 0.544 | 0.543 | 0.545 | 0.35 | 8.36 |
| | 0.4 | 0.494 | 0.497 | 0.498 | 0.496 | 0.35 | 16.49 |
| | 0.6 | 0.445 | 0.453 | 0.443 | 0.447 | 0.89 | 24.79 |
| | 1 | 0.357 | 0.344 | 0.35 | 0.35 | 1.09 | 41.05 |
| | 2 | 0.208 | 0.195 | 0.195 | 0.199 | 1.26 | 66.46 |
| | 5 | 0.018 | 0.01 | 0.009 | 0.012 | 0.73 | 98.82 |

Experimental Example 1-2: Evaluation of Anti-Inflammatory Effect (NO Inhibitory Ability)

When mammals receive an inflammatory stimulus, they synthesize NO (nitric oxide) by macrophages, which is a neurotransmitter that dilates blood vessels and suppresses inflammation.

Therefore, in order to check an effect of inhibiting NO radicals, the sample was mixed with 10 mM sodium nitroferricyanide dihydrate and reacted at 25° C. for 150 minutes. After aliquoting 0.5 mL each, 1 mL of 1% sulfanylamine was added, and the mixture reacted at room temperature for 10 minutes. After the reaction, 2 mL of 0.1% N-(1-naphthyl) ethylenediamine dihydrochloride was mixed, and the mixture was reacted at room temperature for 30 minutes. Then, absorbance was measured at 540 nm. A NO radical scavenging ability (%) was calculated using the following formula, and the results are shown in [Table 8].

NO Radical Scavenging Ability (%)=(Absorbance of Test Group/Absorbance of Untreated Group)× 100

TABLE 8

Evaluation result of anti-inflammatory effect (inhibition rate of NO production)

| Sample | Test Concentration | Inhibition rate of NO production (%) |
|---|---|---|
| Example 1 | 50 mg/mL | 44.59 |
| Example 2 | 50 mg/mL | 32.09 |
| Example 3 | 50 mg/mL | 80.22 |
| Example 4 | 1 mg/mL | 53.01 |
| Example 5 | 1 mg/mL | 30.24 |
| Example 6 | 1 mg/mL | 43.58 |
| Example 7 | 1 mg/mL | 74.18 |
| Example 8 | 1 mg/mL | 59.85 |
| Example 9 | 1 mg/mL | 53.44 |
| Example 14 | 1 mg/mL | 54.35 |
| Example 15 | 1 mg/mL | 59.33 |
| Example 16 | 1 mg/mL | 66.67 |

In addition, the minimum inhibitory concentration (IC 50, mg/ml) that inhibits the activity of NO radicals by 50% for Examples 4 to 6 (Cultures 1 to 3) was evaluated. As shown in [Table 9] to [Table 11], NO radical scavenging effects were excellent even at low concentrations of 0.80 mg/ml, 3.19 mg/ml and 1.41 mg/ml in Examples 4 to 6, respectively.

TABLE 9

Evaluation Result of Anti-inflammatory Effect by Concentration of Culture 1 (Example 4)

| Sample | Concentration (mg/mL) | O.D. 734 nm | | | Average | Standard Deviation (%) | Inhibition Rate (%) |
|---|---|---|---|---|---|---|---|
| Untreated Group | — | 0.113 | 0.116 | 0.12 | 0.116 | — | — |
| Example 4 | 0.1 | 0.096 | 0.098 | 0.089 | 0.094 | 4.06 | 18.91 |
| | 0.2 | 0.081 | 0.078 | 0.078 | 0.079 | 1.49 | 32.09 |
| | 0.4 | 0.071 | 0.068 | 0.071 | 0.07 | 1.49 | 39.83 |
| | 0.6 | 0.058 | 0.049 | 0.068 | 0.058 | 8.17 | 49.86 |
| | 1 | 0.05 | 0.06 | 0.054 | 0.055 | 4.33 | 53.01 |
| | 2 | 0.057 | 0.046 | 0.047 | 0.05 | 5.23 | 57.02 |
| | 5 | 0.036 | 0.043 | 0.036 | 0.038 | 3.47 | 67.05 |

TABLE 10

Evaluation Result of Anti-inflammatory Effect by Concentration of Culture 2 (Example 5)

| Sample | Concentration (mg/mL) | O.D. 734 nm | | | Average | Standard Deviation (%) | Inhibition Rate (%) |
|---|---|---|---|---|---|---|---|
| Untreated Group | — | 0.193 | 0.191 | 0.198 | 0.194 | — | — |
| Example 5 | 0.1 | 0.178 | 0.181 | 0.172 | 0.177 | 2.36 | 8.76 |
| | 0.2 | 0.171 | 0.175 | 0.174 | 0.173 | 1.07 | 10.65 |
| | 0.4 | 0.161 | 0.155 | 0.164 | 0.16 | 2.36 | 17.53 |
| | 0.6 | 0.15 | 0.145 | 0.153 | 0.149 | 2.08 | 23.02 |
| | 1 | 0.138 | 0.135 | 0.133 | 0.135 | 1.3 | 30.24 |
| | 2 | 0.118 | 0.115 | 0.106 | 0.113 | 3.22 | 41.75 |
| | 5 | 0.078 | 0.077 | 0.063 | 0.073 | 4.32 | 62.54 |

TABLE 11

Evaluation Result of Anti-inflammatory Effect by Concentration of Culture 3 (Example 6)

| Sample | Concentration (mg/mL) | O.D. 734 nm | | | Average | Standard Deviation (%) | Inhibition (%) |
|---|---|---|---|---|---|---|---|
| Untreated Group | — | 0.182 | 0.173 | 0.175 | 0.176 | — | — |
| Example 5 | 0.1 | 0.14 | 0.145 | 0.147 | 0.144 | 2.04 | 18.49 |
| | 0.2 | 0.126 | 0.129 | 0.119 | 0.125 | 2.9 | 29.43 |
| | 0.4 | 0.115 | 0.121 | 0.114 | 0.117 | 2.14 | 33.96 |
| | 0.6 | 0.102 | 0.107 | 0.112 | 0.107 | 2.83 | 39.43 |
| | 1 | 0.1 | 0.101 | 0.098 | 0.1 | 0.86 | 43.58 |
| | 2 | 0.077 | 0.068 | 0.073 | 0.073 | 2.55 | 58.87 |
| | 5 | 0.058 | 0.057 | 0.057 | 0.057 | 0.33 | 67.55 |

Experimental Example 1-3: Evaluation of Anti-Inflammatory and Moisturizing Effect (Hyaluronidase Inhibition)

Hyaluronidase is an enzyme that hydrolyzes hyaluronic acid, which is a skin moisturizing factor, and has a function of causing inflammation. An anti-inflammatory effect was evaluated using a method of measuring the anti-inflammatory effect by confirming a degree of inhibition of an activity of hyaluronidase (Y Kakegawa, et al., Japanese J. Inflammation, 4: 437-438, 1984).

The sample was added to 0.1 ml of a hyaluronidase solution (10 mg/ml) dissolved in 1M acetic acid buffer solution (pH 3.5) and reacted at 37° C. for 20 minutes. After 12.5 mM CaCl 2 0.1 ml was added, the mixture was reacted for 20 minutes at 37° C. again. After the reaction, a hyaluronic acid solution (6 mg/ml) dissolved in 0.25 ml of 0.1M acetic acid buffer solution (pH 3.5) was added and reacted for 40 minutes at 37° C., and 0.1 ml of 0.4N NaOH and 0.1 ml of 0.4M potassium tetraborate were added, reacted for 3 minutes at 100° C., and cooled. Then, 2.5 ml of ρ-dimethylaminobenzaldehyde solution was added, and reacted for 20 minutes at 37° C. again to develop color, and absorbance was measured at 540 nm. A hyaluronidase inhibitory ability was calculated using the following formula, and the results are shown in [Table 12].

Hyaluronidase Inhibitory Ability (%)=(Absorbance of Test Group/Absorbance of Untreated Group)×100

TABLE 12

Anti-inflammatory And Moisturizing Effect (Hyaluronidase Inhibition) Evaluation Result

| Sample | Test Concentration | Active Oxygen (ABTs) Scavenging Ability (%) |
|---|---|---|
| Example 1 | 50 mg/mL | 51.19 |
| Example 2 | 50 mg/mL | 52.1 |
| Example 3 | 50 mg/mL | 90.49 |
| Example 4 | 1 mg/mL | 36.13 |
| Example 5 | 1 mg/mL | 44.06 |
| Example 6 | 1 mg/mL | 33.55 |
| Example 7 | 1 mg/mL | 52.85 |
| Example 8 | 1 mg/mL | 33.33 |
| Example 9 | 1 mg/mL | 62.2 |
| Example 10 | 1 mg/mL | 47.32 |
| Example 12 | 1 mg/mL | 55.64 |
| Example 13 | 1 mg/mL | 55.6 |

In addition, a minimum inhibitory concentration (IC 50, mg/ml) that inhibits the activity of hyaluronidase by 50% was evaluated for Examples 4 to 6 (Cultures 1 to 3). As shown in [Table 13] to [Table 15], the hyaluronidase inhibitory effects were excellent even at low concentrations of 1.36 mg/ml, 2.09 mg/ml and 3.99 mg/ml in Examples 4 to 6, respectively.

TABLE 13

Evaluation Result of Hyaluronidase Inhibitory Ability by Concentration of Culture 1 (Example 4)

| Sample | Concentration (mg/mL) | O.D. 734 nm | | | Average | Standard Deviation (%) | Inhibition Rate (%) |
|---|---|---|---|---|---|---|---|
| Untreated Group | — | 0.255 | 0.248 | 0.236 | 0.246 | — | — |
| Example 4 | 0.1 | 0.242 | 0.239 | 0.244 | 0.241 | 1.02 | 1.89 |
| | 0.2 | 0.237 | 0.241 | 0.241 | 0.239 | 0.94 | 2.71 |
| | 0.4 | 0.194 | 0.212 | 0.202 | 0.203 | 3.66 | 17.73 |
| | 0.6 | 0.163 | 0.174 | 0.179 | 0.169 | 3.32 | 30.18 |
| | 1 | 0.158 | 0.169 | 0.145 | 0.164 | 4.88 | 36.13 |
| | 2 | 0.136 | 0.131 | 0.127 | 0.134 | 1.83 | 46.68 |
| | 5 | 0.106 | 0.112 | 0.108 | 0.109 | 1.24 | 55.89 |

TABLE 14

Evaluation Result of Hyaluronidase Inhibitory Ability
by Concentration of Culture 2 (Example 5)

| Sample | Concentration (mg/mL) | O.D. 734 nm | | | Average | Standard Deviation (%) | Inhibition Rate (%) |
|---|---|---|---|---|---|---|---|
| Untreated Group | — | 0.148 | 0.163 | 0.152 | 0.154 | — | — |
| Example 5 | 0.1 | 0.144 | 0.148 | 0.139 | 0.144 | 2.92 | 6.91 |
| | 0.2 | 0.134 | 0.128 | 0.122 | 0.128 | 3.89 | 17.06 |
| | 0.4 | 0.121 | 0.129 | 0.116 | 0.122 | 4.25 | 20.95 |
| | 0.6 | 0.105 | 0.111 | 0.107 | 0.108 | 1.98 | 30.24 |
| | 1 | 0.078 | 0.097 | 0.084 | 0.086 | 6.29 | 44.06 |
| | 2 | 0.073 | 0.079 | 0.081 | 0.078 | 2.7 | 49.68 |
| | 5 | 0.054 | 0.061 | 0.069 | 0.061 | 4.86 | 60.26 |

TABLE 15

Evaluation Result of Hyaluronidase Inhibitory Ability
by Concentration of Culture 3 (Example 6)

| Sample | Concentration (mg/mL) | O.D. 734 nm | | | Average | Standard Deviation (%) | Inhibition Rate (%) |
|---|---|---|---|---|---|---|---|
| Untreated Group | — | 0.145 | 0.157 | 0.151 | 0.151 | — | — |
| Example 5 | 0.1 | 0.153 | 0.149 | 0.15 | 0.151 | 1.38 | 0.22 |
| | 0.2 | 0.142 | 0.148 | 0.139 | 0.143 | 3.03 | 5.3 |
| | 0.4 | 0.132 | 0.141 | 0.128 | 0.134 | 4.41 | 11.48 |
| | 0.6 | 0.119 | 0.108 | 0.121 | 0.116 | 4.64 | 23.18 |
| | 1 | 0.098 | 0.103 | 0.1 | 0.1 | 1.67 | 33.55 |
| | 2 | 0.088 | 0.097 | 0.084 | 0.09 | 4.41 | 40.62 |
| | 5 | 0.071 | 0.063 | 0.071 | 0.068 | 3.06 | 54.75 |

Experimental Example 1-4: Evaluation of
Lightening Effect (Tyrosinase Inhibition)

Tyrosinase is an enzyme that promotes oxidation of tyrosine in the living body and helps to produce melanin. A lightening effect was evaluated by applying a method of measuring a degree of inhibition of forming of a black polymer called melanin, which is caused by tyrosine oxidation by inhibiting the function of this enzyme (Pomerantz S. H.: J. Biochem., 24: 161-168, 1996). A tyrosinase inhibitory activity was measured by modifying a method, such as vagi, of measuring DOPA chrome produced as a result of the action of tyrosinase by a colorimetric method. Specifically, in 2.3 mL of 50 mM sodium phosphate buffer solution (pH 6.8), 0.5 mL of 10 mM L-DOPA, 0.5 mL of 110 unit/ml mushroom tyrosinase, and 20 µl of the sample solution were added, and then reacted at 25° C. for 10 minutes. The absorbance was measured at 475 nm, and a tyrosinase inhibitory ability (%) was calculated using the following formula and shown in [Table 16].

Tyrosinase Inhibitory Ability (%)=(Absorbance of Test Group/Absorbance of Untreated Group)×100

TABLE 16

Evaluation Result of Lightening Effect
(Tyrosinase Inhibitory Ability)

| Sample | Test Concentration | Tyrosinase Inhibitory Ability (%) |
|---|---|---|
| Example 1 | 50 mg/mL | 85.68 |
| Example 3 | 50 mg/mL | 79.61 |
| Example 4 | 1 mg/mL | 44.13 |
| Example 6 | 1 mg/mL | 32.62 |
| Example 7 | 1 mg/mL | 34.13 |
| Example 8 | 1 mg/mL | 24.19 |
| Example 14 | 1 mg/mL | 47.89 |
| Example 15 | 1 mg/mL | 35.04 |

In addition, the minimum inhibitory concentration ($IC_{50}$, mg/ml) that inhibits the activity of tyrosinase by 50% for Examples 4 and 6 (Cultures 1 and 3) was evaluated. As shown in [Table 17] and [Table 18], a tyrosinase inhibitory ability was excellent even at low concentrations of 2.03 mg/ml and 4.16 mg/ml in Examples 4 and 6, respectively.

TABLE 17

Evaluation Result of Tyrosinase Inhibitory Ability
by Concentration of Culture 1 (Example 4)

| Sample | Concentration (mg/mL) | O.D. 734 nm | | | Average | Standard Deviation (%) | Inhibition Rate (%) |
|---|---|---|---|---|---|---|---|
| Untreated Group | — | 0.283 | 0.288 | | 0.285 | — | — |
| Example 4 | 0.1 | 0.267 | 0.279 | | 0.273 | 2.97 | 4.38 |
| | 0.2 | 0.238 | 0.248 | | 0.243 | 2.48 | 14.89 |
| | 0.4 | 0.231 | 0.228 | | 0.23 | 0.74 | 19.61 |
| | 0.6 | 0.201 | 0.198 | 0.2 | | 0.74 | 30.12 |
| | 1 | 0.156 | 0.163 | | 0.16 | 1.73 | 44.13 |
| | 2 | 0.142 | 0.144 | | 0.143 | 0.5 | 49.91 |
| | 5 | 0.111 | 0.126 | | 0.119 | 3.72 | 58.49 |

TABLE 18

Evaluation Result of Tyrosinase Inhibitory Ability
by Concentration of Culture 3 (Example 6)

| Sample | Concentration (mg/mL) | O.D. 734 nm | | | Average | Standard Deviation (%) | Inhibition Rate (%) |
|---|---|---|---|---|---|---|---|
| Untreated Group | — | 0.451 | 0.461 | 0.443 | 0.451 | — | — |
| Example 5 | 0.1 | 0.437 | 0.444 | 0.451 | 0.444 | 1.55 | 1.7 |
| | 0.2 | 0.422 | 0.417 | 0.423 | 0.421 | 0.71 | 6.86 |
| | 0.4 | 0.377 | 0.383 | 0.384 | 0.381 | 0.84 | 15.57 |
| | 0.6 | 0.334 | 0.34 | 0.349 | 0.341 | 1.67 | 24.5 |
| | 1 | 0.317 | 0.299 | 0.297 | 0.304 | 2.44 | 32.62 |
| | 2 | 0.268 | 0.279 | 0.259 | 0.269 | 2.22 | 40.52 |
| | 5 | 0.196 | 0.222 | 0.21 | 0.209 | 2.88 | 53.65 |

Experimental Example 1-5: Evaluation of Elasticity
and Wrinkle Improvement Effect (Collagenase
Inhibition)

Collagenase is known to be an enzyme that decomposes collagen, and its expression is greatly increased by irradiation with ultraviolet rays. Collagenase is a major cause of reduction and degeneration of collagen by ultraviolet rays and is a major cause of skin wrinkle formation. Using the fact that collagenase is the main factor of skin problems, a collagenase inhibitory effect was measured for the test group, and elasticity and wrinkle improvement effects were evaluated.

The collagenase enzyme activity inhibition experiment was performed using the azochol method using azocoll, which is a dye for collagen. In order to measure the enzyme inhibitory activity, 4 mM $CaCl_2$ was added to 0.25 mL of 0.1M Tris-HCl buffer solution (pH 7.5) in 0.1 mL of the sample. After adding a substrate solution dissolved with 4-phenylazobenzyloxycarbonyl-Pro-Leu-Gly-Pro-Arg (0.3 mg/ml) and 0.15 mL of collagenase (0.2 mg/ml) enzyme solution, the mixture was reacted at room temperature for 20 minutes. Then, 0.5 mL of 6% citric acid and 2.5 mL of ethyl acetate were added in order, and absorbance was measured at 320 nm. The collagenase inhibitory ability (%) was calculated using the following formula, and the results are shown in [Table 19].

Collagenase Inhibitory Ability (%)=(Absorbance of Test Group/Absorbance of Untreated Group)× 100

TABLE 19

Evaluation Result of Elasticity and Wrinkle Improvement Effect (Collagenase Inhibition Ability) (Example 4)

| Sample | Test Concentration | Collagenase Inhibitory Ability (%) |
|---|---|---|
| Example 1 | 50 mg/mL | 79.33 |
| Example 3 | 50 mg/mL | 93.44 |
| Example 4 | 1 mg/mL | 36.73 |
| Example 6 | 1 mg/mL | 25.95 |
| Example 7 | 1 mg/mL | 33.36 |
| Example 8 | 1 mg/mL | 31.75 |
| Example 14 | 1 mg/mL | 25.36 |
| Example 15 | 1 mg/mL | 21.7 |

In addition, the minimum inhibitory concentration (IC 50, mg/ml) that inhibits the activity of collagenase by 50% for Examples 4 and 6 (Cultures 1 and 3) was evaluated. As shown in [Table 20] to [Table 21], elasticity and wrinkle improvement effect were excellent even at low concentrations of 3.12 mg/ml and 4.78 mg/ml in Examples 4 and 6, respectively.

TABLE 20

Evaluation Result of Elasticity and Wrinkle Improvement Effect by Concentration of Culture 1 (Collagenase Inhibition Ability) (Example 4)

| Sample | Concentration (mg/mL) | O.D. 734 nm | | Average | Standard Deviation (%) | Inhibition Rate (%) |
|---|---|---|---|---|---|---|
| Untreated Group | — | 0.283 | 0.288 | 0.285 | — | — |
| Example 4 | 0.1 | 0.267 | 0.279 | 0.273 | 2.97 | 4.38 |
| | 0.2 | 0.238 | 0.248 | 0.243 | 2.48 | 14.89 |
| | 0.4 | 0.231 | 0.228 | 0.23 | 0.74 | 19.61 |
| | 0.6 | 0.201 | 0.198 | 0.2 | 0.74 | 30.12 |
| | 1 | 0.156 | 0.163 | 0.16 | 1.73 | 44.13 |
| | 2 | 0.142 | 0.144 | 0.143 | 0.5 | 49.91 |
| | 5 | 0.111 | 0.126 | 0.119 | 3.72 | 58.49 |

TABLE 21

Evaluation Result of Elasticity and Wrinkle Improvement Effect by Concentration of Culture 3 (Collagenase Inhibition Ability) (Example 6)

| Sample | Concentration (mg/mL) | O.D. 734 nm | | | Average | Standard Deviation (%) | Inhibition Rate (%) |
|---|---|---|---|---|---|---|---|
| Untreated Group | — | 0.287 | 0.292 | 0.288 | 0.289 | — | — |
| Example 5 | 0.1 | 0.274 | 0.282 | 0.288 | 0.281 | 2.43 | 2.65 |
| | 0.2 | 0.269 | 0.274 | 0.279 | 0.274 | 1.73 | 5.19 |
| | 0.4 | 0.258 | 0.263 | 0.253 | 0.258 | 1.73 | 10.73 |
| | 0.6 | 0.224 | 0.232 | 0.248 | 0.235 | 4.23 | 18.8 |
| | 1 | 0.219 | 0.214 | 0.209 | 0.214 | 1.73 | 25.95 |
| | 2 | 0.178 | 0.183 | 0.181 | 0.181 | 0.87 | 37.49 |
| | 5 | 0.147 | 0.135 | 0.143 | 0.142 | 2.11 | 50.98 |

Experimental Example 2: Evaluation of Efficacy in Cells In Vitro

In order to verify an overall effectiveness of a composition of Example 7 on skin aging improvement at a cellular level, cytotoxicity, wrinkle improvement (mRNA expression of MMP-1 using Hs68 cells, ATCC, and real-time PCR), lightening improvement (B16F10 cells, Korean Cell Line Bank, melanin content confirmation), moisturizing improvement (HAS-2 expression confirmation using HaCaT cells, ATCC, and real-time PCR), and anti-inflammatory improvement (mRNA expression of iNOS using RAW264.7 cells, Korean Cell Line Bank, NO Production inhibition ability, and real-time PCR) were evaluated. As a result, at a concentration of 1,000 μg/ml or less, cytotoxicity was not observed, and it was confirmed that the effect of improving skin aging was excellent through inhibiting MMP-1 mRNA expression, reducing melanin production, promoting HAS-2 expression, inhibiting NO production, and inhibiting iNOS mRNA expression. Significance was verified with an independent sample student t-test, and when the p-value was less than 0.05, it was determined that there was a statistically significant difference. The experimental procedure and evaluation results are as follows.

Experimental Example 2-1: Evaluation of Wrinkle Improvement Effect (Inhibition of MMP1 Expression)

Skin aging is caused by a structural change in the extracellular matrix existing in the dermal layer of skin. Specifically, skin aging is caused by a decrease in collagen, a protein that is a skin elasticity component in the dermal tissue of the skin. Extracellular matrix degradation occurs by matrix-metalloproteinases (MMPs), and collagen degradation occurs by MMP-1, thereby causing wrinkles. As a result of evaluating an efficacy through MMP-1 expression inhibition ability, cytotoxicity was not observed at the concentration of 1,000 μg/ml and less, and it significantly decreases at the concentration of 600 to 1,000 μg/ml, and 52.63% MMP-1 mRNA expression was inhibited at the concentration of 1,000 μg/ml.

1-1) Cell Culture

Hs68 cells used in the experiment were purchased from ATCC. The 10% FBS and 1% Penicillin/streptomycin were added to DMEM medium and cultured in an incubator at 37° C. under 90% of relative humidity and 5% of $CO_2$.

1-2) Cell Viability

Hs68 cells were cultured in 96-well plates at a concentration of $5 \times 10^3$ cells/well for 24 hours. The samples were treated by each concentration and cultured for 24 hours. The 10 µl of MTT solution (5 mg/ml) was added for each sample and further incubated for 4 hours. After removing supernatant, 100 µl of dimethyl sulfoxide (DMSO) was added, and absorbance were measured at 570 nm. Cell viability was calculated according to the following formula.

Cell Viability (%)=(Absorbance in Sample Added Group/Absorbance in Sample Not Added Group)×100

1-3) Real-Time PCR

Real-time PCR was performed to confirm mRNA expression of MMP-1 in Hs68 cells. Hs68 cells were aliquoted to a volume of $5 \times 10^5$ cells/well in a 60 mm plate and cultured for 24 hours in an incubator at 37° C. under 5% of $CO_2$. Example 1 was treated for 45 minutes by concentration, treated with TNF-α (20 ng/ml, and reacted for 24 hours, and then, supernatant was removed. Cells were dissolved using Trizol reagent (Ambion, USA). cDNA was synthesized according to manufacturing instructions of Revertra ACE-α- (Toyobo, Japan). The real-time PCR for synthesized cDNA was conducted using GAPDH (Hs02786624_g1), MMP1 (Hs00899658_m1) primers, and Taqman master mix (Thermo fisher, USA).

Figure 1B:
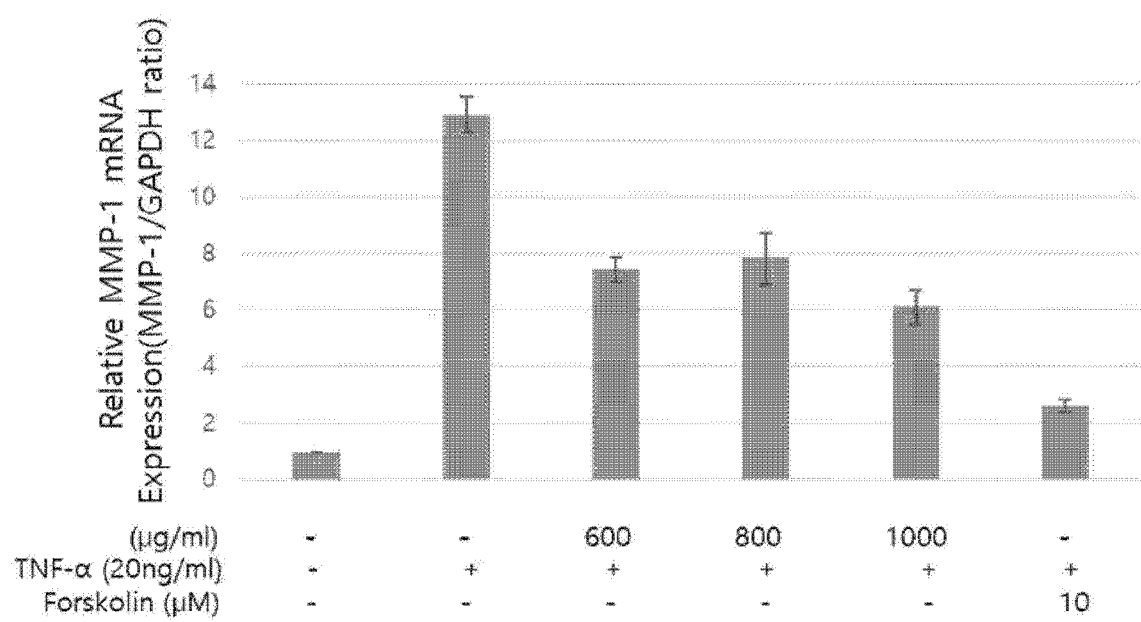
FIG. 1*b* shows a confirmation result of an MMP expression inhibitory ability.

FIG. 1a shows a confirmation result of cytotoxicity in Hs68 cells, and FIG. 1b shows a confirmation result of an MMP expression inhibitory ability.

Experimental Example 2-2 Evaluation of Lightening Effect (Inhibition of Melanin Production)

Skin darkening is caused by increased melanogenesis in melanocytes present in the skin. Through external stimuli such as UV exposure, melanin forming cells synthesize melanin from L-tyrosine, and several enzymes are involved in this process. In order to promote melanin synthesis in B16F10 cells, α-MSH (200 nM), which is a melanogenesis stimulating hormone, was treated, and a lightening effect was evaluated by confirming a decrease in melanin content. Cytotoxicity was not observed at a concentration of 1,000 µg/ml or less, and the melanin content significantly decreased at a concentration of 600 to 1,000 µg/ml, and melanin production was inhibited by 46.69% at a concentration of 1,000 µg/ml.

1-1) Cell Culture

B16F10 cells used in the experiment were purchased from the Korean Cell Line Bank. The 10% FBS and 1% Penicillin/streptomycin were added to DMEM medium and cultured in an incubator at 37° C. under 90% of relative humidity and 5% of $CO_2$.

1-2) Cell Viability

*B16F10 cells were aliquoted in a 96-well plate at a concentration of $4 \times 10^3$ cells/well and cultured for 24 hours. After incubation for 24 hours, α-MSH (200 nM) and samples were treated for each concentration and cultured for 72 hours. MTT solution (5 mg/ml) was added for each 10 µl and further incubated for 4 hours. Then, the medium was removed, 100 µl of dimethyl sulfoxide (DMSO) was added, and the absorbance was measured at 570 nm. Cell viability was calculated according to the following formula.

Cell Viability (%)=(Absorbance in Sample Added Group/Absorbance in Sample Not Added Group)×100

1-3) Melanin Content

B16F10 cells were aliquoted in a 6-well plate at a concentration of $4 \times 10^4$ cells/well and cultured for 24 hours. α-MSH at a concentration of 200 nM was co-treated with the sample, and melanin synthesis was promoted for 72 hours. After 72 hours, the cultured cells were treated with trypsin/EDTA and centrifuged. After reacting at 80° C. for 1 hour using 1N of NaOH, absorbance was measured at 405 nm.

Figure 2A:
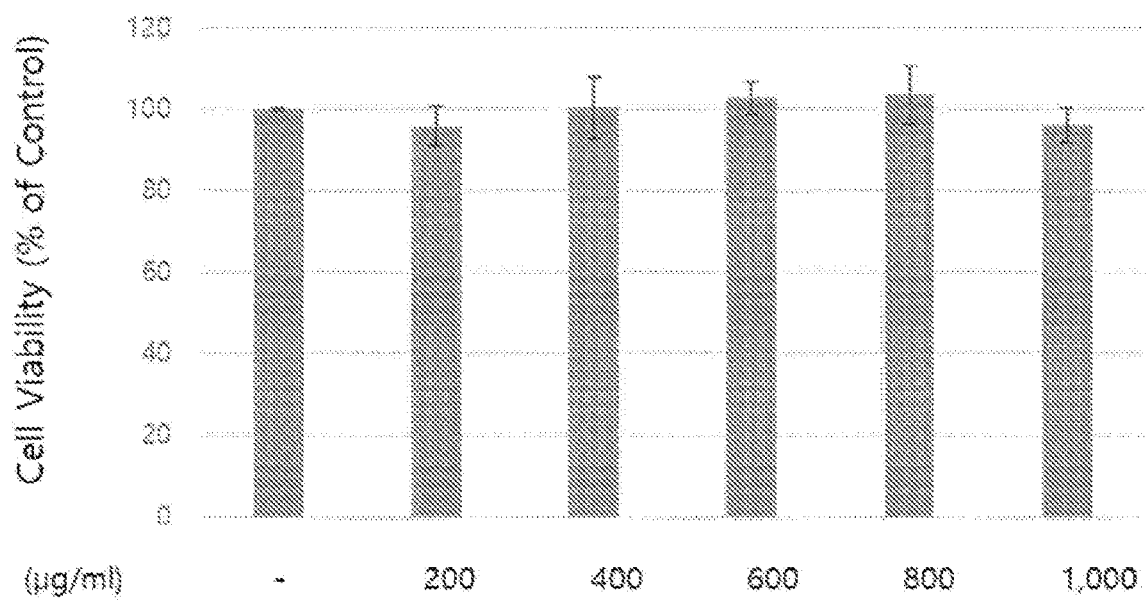
FIG. 2*a* shows a measurement result of cytotoxicity, cell viability, in B16F10 cells for a composition of Example 7 of the present invention.
Figure 2B:
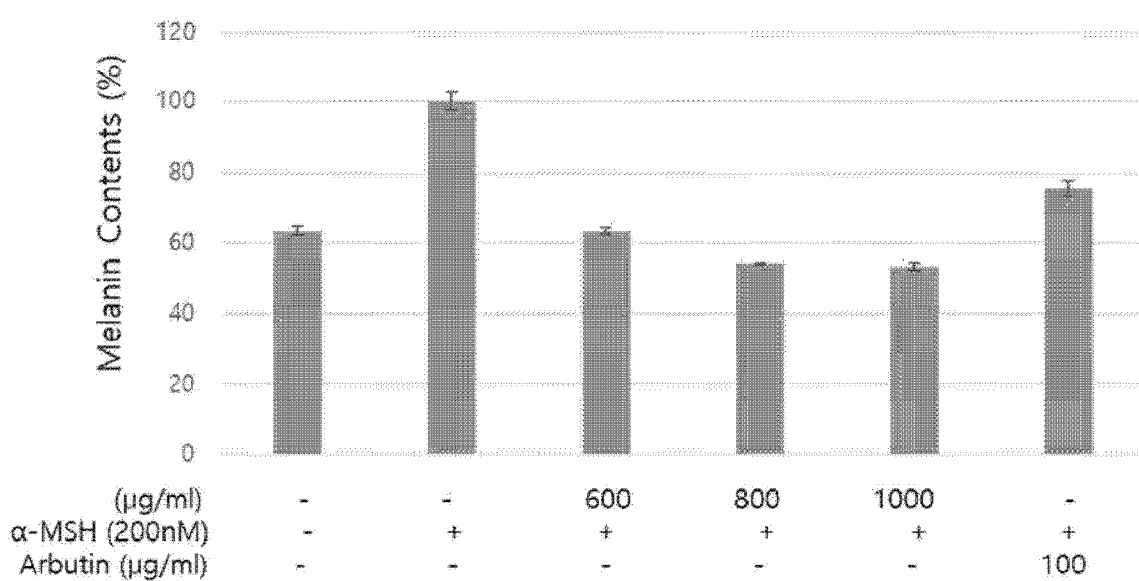
FIG. 2*b* shows an amount of melanin production, melanin content, in B16F10 cells.

FIG. 2a shows a measurement result of cytotoxicity (cell viability) in B16F10 cells, and FIG. 2b shows an amount of melanin production (melanin content) in B16F10 cells.

Experimental Example 2-3: Evaluation of Moisturizing Effect (Increase in Has-2 Expression)

*In order for skin barrier to work smoothly, various types of lipids, sugars, and proteins are involved and interact with each other. Among them, hyaluronic acid (HA) is a high molecular weight glycosaminoglycan present in the extracellular connective tissue and acts as a barrier to prevent water evaporation. It is known that the content of HA decreases with age, and the decrease in the content of HA due to these intrinsic or extrinsic factors causes factors of a decrease in skin elasticity, rough skin, wrinkles, and the like. Using the fact that HA content is controlled by continuous synthesis by hyaluronic acid synthase (HAS) and degradation by hyaluronidase (HYAL), the moisturizing effect was evaluated through increased HAS-2 expression. As a result, it was confirmed that cytotoxicity was not observed at a concentration of 1,000 µg/ml or less, HAS-2 expression significantly increased at a concentration of 600 to 1,000 µg/ml, and HAS-2 mRNA expression increased by 54% at a concentration of 1,000 µg/ml.

1-1) Cell Culture

HaCaT cells used in the experiment were purchased from ATCC. The 10% FBS and 1% Penicillin/streptomycin were added to DMEM medium and cultured in an incubator at 37° C. under 90% of relative humidity and 5% of $CO_2$.

1-2) Cell Viability

HaCaT cells were aliquoted in a 96-well plate at a concentration of $1 \times 10^5$ cells/well and cultured for 24 hours. Samples were treated for each concentration and incubated for 24 hours. The 10 µl of MTT solution (5 mg/ml) was added for each sample and further incubated for 4 hours. After removing the medium, 100 µl of Dimethyl Sulfoxide (DMSO) was added, and absorbance was measured at 570 nm. Cell viability was calculated according to the following formula.

Cell Viability (%)=(Absorbance in Sample Added Group/Absorbance in Sample Not Added Group)×100

1-3) Real-Time PCR

Real-time PCR was performed to confirm an mRNA expression of HAS-2 in HaCaT cells. HaCaT cells were aliquoted in a 60 mm plate to be a $6 \times 10^5$ cells/well and cultured for 24 hours in an incubator at 37° C. under 5% of $CO_2$. After the samples were treated for 24 hours at each concentration, the supernatant was removed. The treated cells were dissolved using Trizol reagent (Ambion, USA). cDNA was synthesized according to the manufacturing instructions of Revertra ACE-α- (Toyobo, Japan). Real-time PCR for synthesized cDNA was conducted using GAPDH (Hs02786624_g1), HAS-2 (Hs00193435_m1) primers, and Taqman master mix (Thermo fisher, USA). As a result, cytotoxicity was not observed at a concentration of 1,000

μg/ml or less, and an increase in HAS-2 mRNA expression was confirmed to be 1.54% at a concentration of 1,000 μg/ml, and a production increase rate of 54% was observed.

Figure 3A:
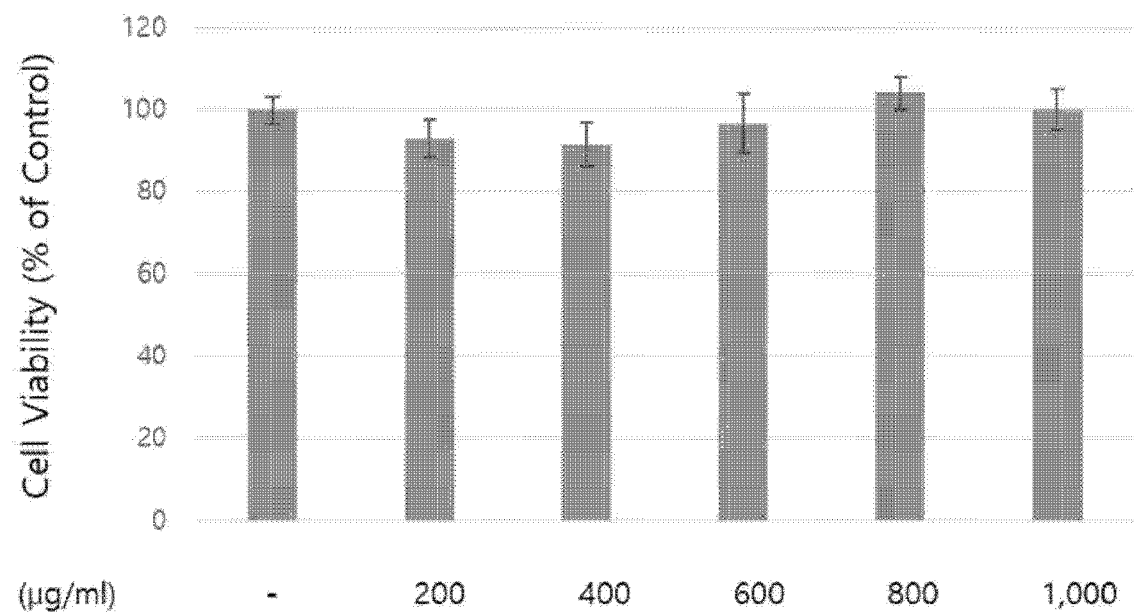
FIG. 3*a* shows a confirmation result of cytotoxicity, cell viability, in HaCaT cells for the composition of Example 7 of the present invention.
Figure 3B:
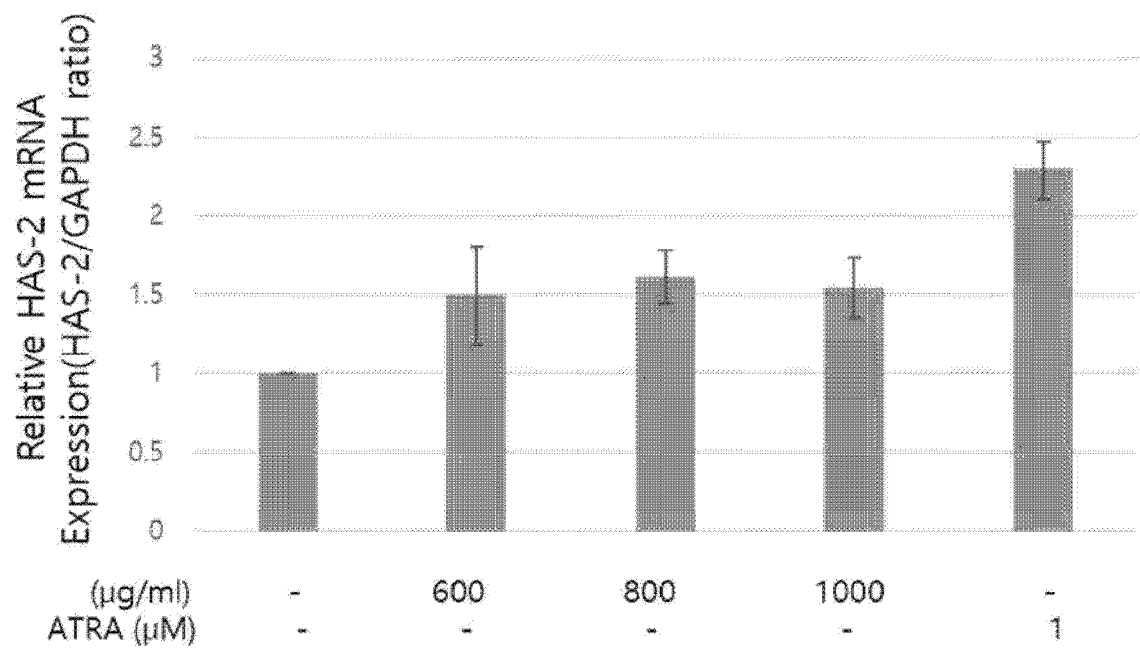
FIG. 3*b* shows an HAS-2 expression degree in HaCaT cells.

FIG. 3a shows a confirmation result of cytotoxicity (cell viability) in HaCaT cells, and FIG. 3b shows an HAS-2 expression degree in HaCaT cells.

Experimental Example 2-4: Evaluation of Anti-inflammatory Effect (Inhibition of NO Production and Inhibition of iNOS Expression)

In order to evaluate an ability to inhibit NO production leading to autoimmune diseases and inflammatory diseases, RAW 264.7 cells were treated with LPS, which is an inflammatory mediator, to significantly increase NO production, and an anti-inflammatory efficacy through inhibition of NO production and iNOS expression of samples was evaluated. As a result, cytotoxicity was not observed at a concentration of 1,000 μg/ml or less, NO production was significantly reduced at a concentration of 400 μg/ml to 1,000 μg/ml, and NO production was reduced by 61.57% at a concentration of 1,000 μg/ml. In addition, iNOS mRNA expression was significantly decreased at a concentration of 600 μg/ml to 1,000 μg/ml, and iNOS mRNA expression was reduced by 50.40% at a concentration of 1,000 μg/ml.

1-1) Cell Culture

RAW 264.7 cells used in the experiment were purchased from the Korean Cell Line Bank and used by adding 10% FBS and 1% Penicillin/streptomycin to DMEM medium.

1-2) Cell Viability

RAW 264.7 cells were cultured in 96-well plates at a concentration of $5 \times 10^4$ cells/well for 24 hours. Samples were treated by concentration and incubated for 24 hours. 10 μl of MTT solution (5 mg/ml) was added for each and further incubated for 4 hours. After removing the supernatant, 100 μl of dimethyl sulfoxide (DMSO) was added, and the absorbance was measured at 570 nm. Cell viability was calculated according to the following formula.

Cell Viability (%)=(Absorbance in Sample Added Group/Absorbance in Sample Not Added Group)×100

1-3) Inhibition of NO Production

RAW 264.7 cells were aliquoted in a 96-well plate at a concentration of $5 \times 10^4$ cells/well and cultured in DMEM medium containing 10% of FBS for 24 hours. The medium was removed, and LPS was treated at a concentration of 1 μg/ml together with samples diluted by each concentration in DMEM (serum free) medium and cultured for 24 hours again. Griess reagent of the same amount as 100 ml of the culture supernatant was added, and the absorbance was measured at 540 nm after reaction for 10 minutes.

NO Production Inhibitory Ability (%)=(Absorbance of Sample Added Group/Absorbance of Sample Not Added Group)×100

1-4) Real-Time PCR

Real-time PCR was performed to confirm the mRNA expression of iNOS in RAW 264.7 cells. RAW 264.7 cells were aliquoted to $5 \times 10^5$ cells/well in a 6-well plate and cultured in an incubator at 37° C. under 5% of $CO_2$ for 24 hours. After the samples were treated for 24 hours at different concentrations, the supernatant was removed. Cells were dissolved using Trizol reagent (Ambion, USA). cDNA was synthesized according to the manufacturing instructions of Revertra ACE-α- (Toyobo, Japan). Real-time PCR for the synthesized cDNA was conducted using GAPDH (Mm99999915_g1), iNOS (Mm00440502_m1), primers, and Taqman master mix (Thermo fisher, USA).

Figure 4A:
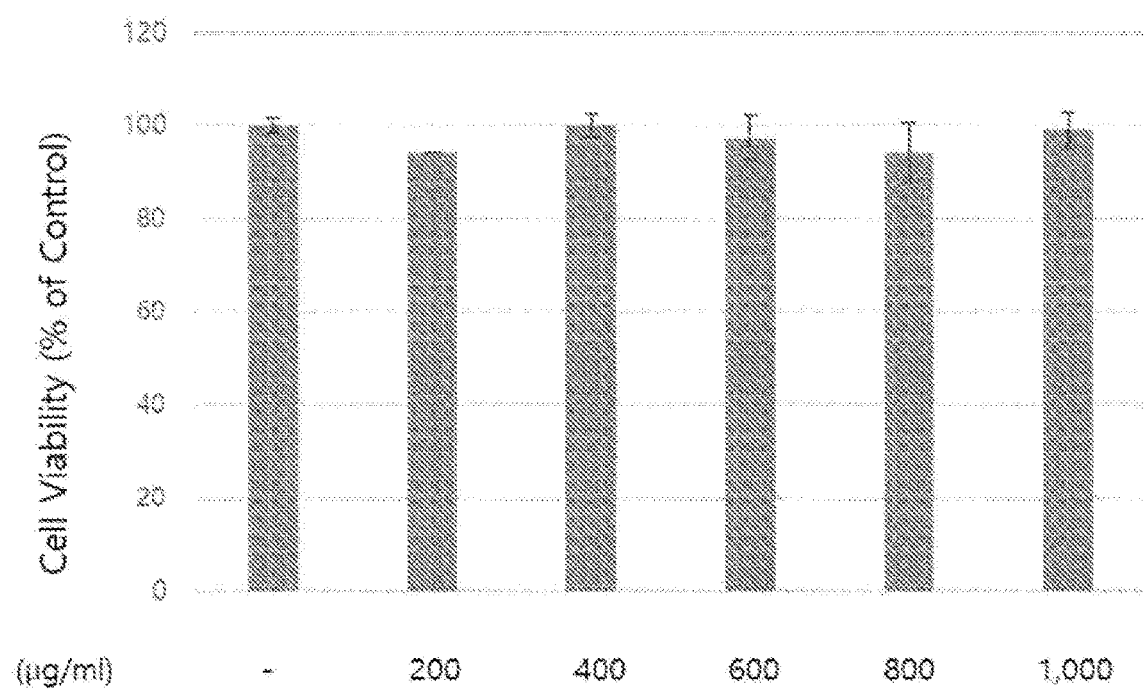
FIG. 4*a* shows a confirmation result of cytotoxicity, cell viability, in RAW 264.7 cells for a composition of Example 7 of the present invention.
Figure 4B:
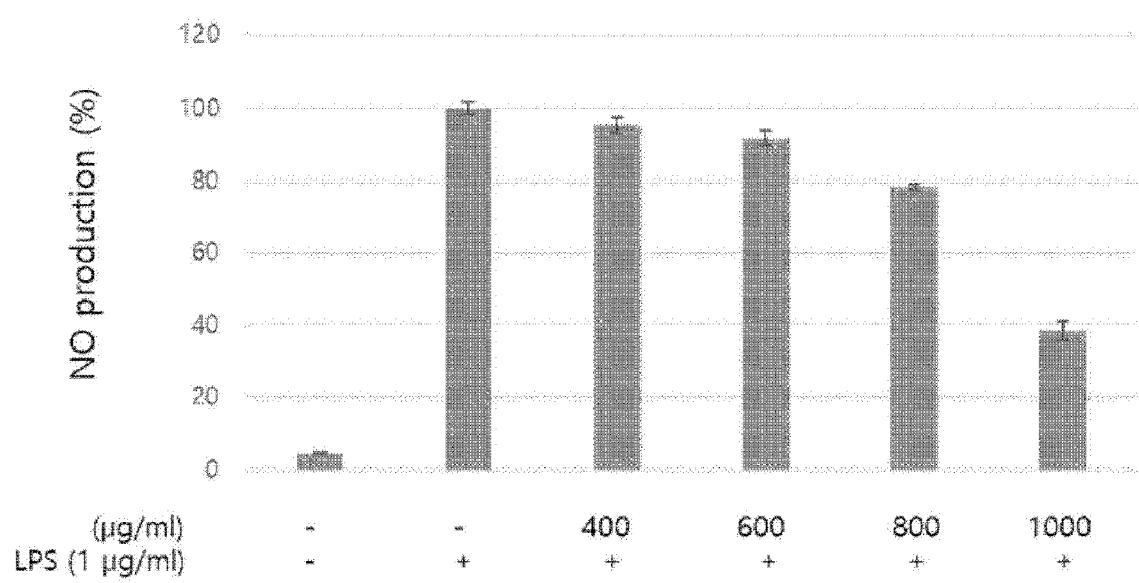
FIG. 4*b* shows a NO production inhibitory ability in RAW 264.7 cells.
Figure 4C:
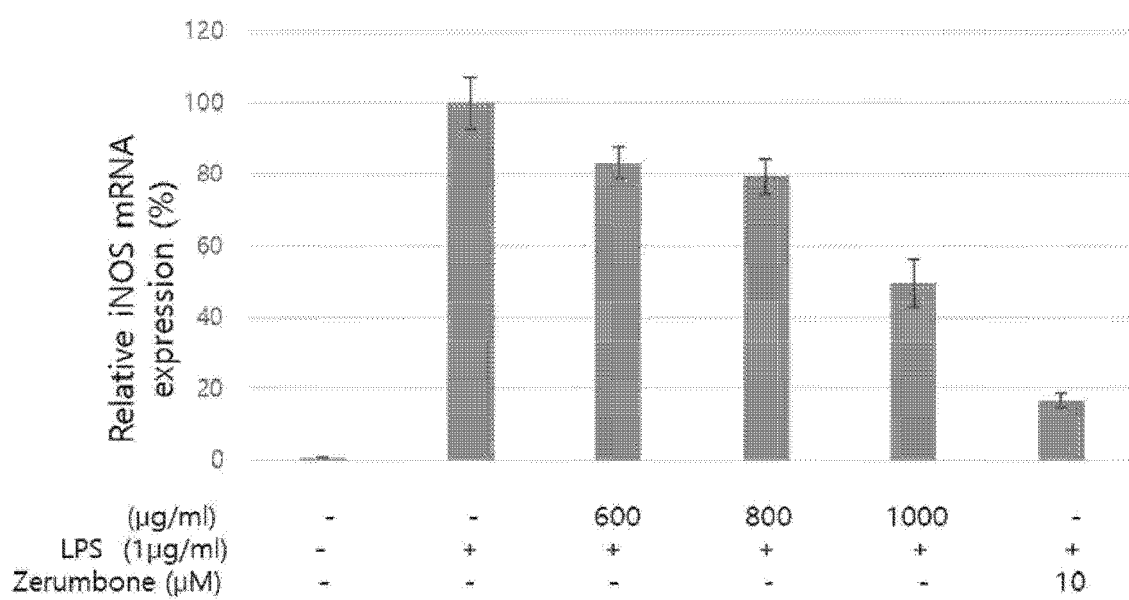
FIG. 4*c* shows a confirmation result of an iNOS expression inhibitory activity.

FIG. 4a shows a confirmation result of cytotoxicity, cell viability, in RAW 264.7 cells for a composition of Example 7 of the present invention, FIG. 4b shows a NO production inhibitory ability in RAW 264.7 cells, and FIG. 4c shows a confirmation result of an iNOS expression inhibitory activity.

Preparation Example 4: Preparation of Solid Powder of Mixed Composition of Dead Cells and Cultures of Lactic Acid Bacteria The mixed compositions of Examples 7 and 8 prepared in Preparation Example 3 were spray-dried with a spray dryer (Buchi Co. B-290, Swiss, Inlet 160° C., Outlet 100° C., Pump 10%, Aspirator 100%)), respectively, and solid powder of a mixture composition of lactic acid bacteria dead cells and cultures was obtained. The composition (weight ratio) is shown in [Table 22] below.

TABLE 22

Solid Powder Composition of Mixed Composition of Lactic Acid Bacteria Dead Cells and Cultures

| Example Component | Example 18 | Example 18 | Comparative Example 1 | Comparative Example 2 |
|---|---|---|---|---|
| Maltodextrin | 25.00 | 0.00 | 15.00 | 0.00 |
| Isomalt | 0.00 | 15.00 | 0 | 25.00 |
| Phospholipid | 0.25 | 0.15 | 0 | 0.00 |
| Example 7 | 0.25 | 0.00 | 1.50 | 0.00 |
| Example 8 | 0.00 | 0.85 | 0.00 | 0.50 |
| Purified water | 74.5 | 84.00 | 83.5 | 74.5 |
| Total | 100.00 | 100.00 | 100.00 | 100.00 |

Preparation Example 5: Preparation of Liquid Polymersome Composition of Dead Cells and Cultures of Lactic Acid Bacteria A probiotic liquid polymersome material was obtained from the mixed composition of Example 7 prepared in Preparation Example 3 by a high-pressure dispersion process using a high-pressure disperser (Suflux, NLM 100, 10000 bar, 60° C.). The composition (weight ratio) of liquid polymersome is shown in Table 23 below.

TABLE 23

Composition of Liquid Polymersome Composition

| Component | Example 20 | Comparative Example 3 | Comparative Example 4 |
|---|---|---|---|
| Purified water | 88.95 | 88.95 | 89.95 |
| *Tamarindus Indica* Seed Polysaccharide | 0.05 | 0.00 | 0.05 |
| Xanthan Gum | 0.00 | 0.05 | 0.00 |
| Butylene Glycol | 6.00 | 6.00 | 6.00 |
| 1,2-Hexanediol | 3.00 | 3.00 | 3.00 |
| Phospholipid | 0.50 | 0.50 | 0.00 |
| Polyglyceryl-6 oleate | 0.5.00 | 0.50 | 0.00 |
| Example 7 | 1.00 | 1.00 | 1.00 |
| Total | 100.00 | 100.00 | 100.00 |

Experimental Example 3: Evaluation of Stability

Phase stability (discoloration, odor, phase separation, and others) according to temperature conditions was evaluated for the solid powder composition prepared in Preparation Example 4 and the liquid polymersome composition prepared in Preparation Example 5, and the results are shown in Table 24 below.

As shown in [Table 24], the solid powder composition was confirmed to be stable when it contained maltodextrin and isomalt as excipients and phospholipids as stabilizers, and the liquid polymersome composition was confirmed to be stable when it contained tamarind seed polysaccharide and phospholipids and polyglyceryl-6 oleate as stabilizers.

TABLE 24

Stability Evaluation Result of Solid Powder and Liquid Polymersome Compositions

| Example | | After 1 Day | After 1 Week | After 2 Week | After 4 Week |
|---|---|---|---|---|---|
| Example 18 | Room Temperature | ◎ | ◎ | ◎ | ◎ |
|  | 50° C. | ◎ | ◎ | ◎ | ◎ |
|  | 4° C. | ◎ | ◎ | ◎ | ◎ |
| Example 19 | Room Temperature | ◎ | ◎ | ◎ | ◎ |
|  | 50° C. | ◎ | ◎ | ◎ | ○ |
|  | 4° C. | ◎ | ◎ | ◎ | ◎ |
| Comparative Example 1 | Room Temperature | ◎ | ○ | ○ | ▲ |
|  | 50° C. | ○ | ▲ | ▲ | ▲ |
|  | 4° C. | ◎ | ○ | ○ | ○ |
| Comparative Example 2 | Room Temperature | ○ | ○ | ▲ | ▲ |
|  | 50° C. | ○ | ▲ | ▲ | ▲ |
|  | 4° C. | ◎ | ○ | ○ | ▲ |
| Example 20 | Room Temperature | ◎ | ◎ | ◎ | ◎ |
|  | 50° C. | ◎ | ◎ | ◎ | ◎ |
|  | 4° C. | ◎ | ◎ | ◎ | ◎ |
| Comparative Example 3 | Room Temperature | ◎ | ○ | ▲ | ▲ |
|  | 50° C. | ◎ | ★ | ★ | ★ |
|  | 4° C. | ◎ | ○ | ▲ | ▲ |
| Comparative Example 4 | Room Temperature | ◎ | ○ | ▲ | ★ |
|  | 50° C. | ◎ | ★ | ★ | ★★ |
|  | 4° C. | ◎ | ○ | ▲ | ▲ |

Stability evaluation criteria ◎: No discoloration, ○: Light yellow discoloration, ▲: Yellow discoloration and odor, ★: Phase separation, ★★: Phase separation, discoloration, and odor

Preparation Example 6: Preparation of Cream Cosmetic Containing Dead Cells and Cultures of Lactic Acid Bacteria Cream cosmetics were prepared from the solid powder material of Example 18 prepared in Preparation Example 4 by an emulsion emulsification process using an emulsifier (T.K. Homo Mixer MarkII, Model 2.5, 3,000 rpm, 75° C.). The composition (weight ratio) is shown in [Table 25] below.

TABLE 25

Composition of Cream Cosmetic

| Type | Component | Example 21 (%) | Comparative Example 5 (%) |
|---|---|---|---|
| Aqueous Phase | 1. Purified water | To 100 | To 100 |
|  | 2. EDTA-2Na | 0.05 | 0.05 |
|  | 3. Glycerin | 10.00 | 10.00 |
|  | 4. 1,3-butylene glycol | 10.00 | 10.00 |
|  | 5. Niacinamide | 2.00 | 2.00 |
|  | 6. Carbomer | 0.20 | 0.20 |
|  | 7. Xanthan Gum | 0.05 | 0.05 |
| Oil Phase | 8. Cetostearyl alcohol | 2.50 | 2.5 |
|  | 9. Arachidyl Alcohol, Behenyl Alcohol, Arachidyl Glucoside | 2.00 | 2.00 |
|  | 10. Self-emulsifying glycerin momostearate | 1.00 | 1.00 |
|  | 11. Hydrogenated Polydecene | 5.00 | 5.00 |
|  | 12. Ethylhexyl-isononanoate | 5.00 | 5.00 |
|  | 13. Cyclomethicone | 5.00 | 5.00 |
| Addition | 12. Neutralizing Agent | Appropriate Amount | Appropriate Amount |
|  | 13. Fragrance and sterilization preservative | Appropriate Amount | Appropriate Amount |
|  | 14. Example 18 | 3.00 | 3.00 |

Figure 5:
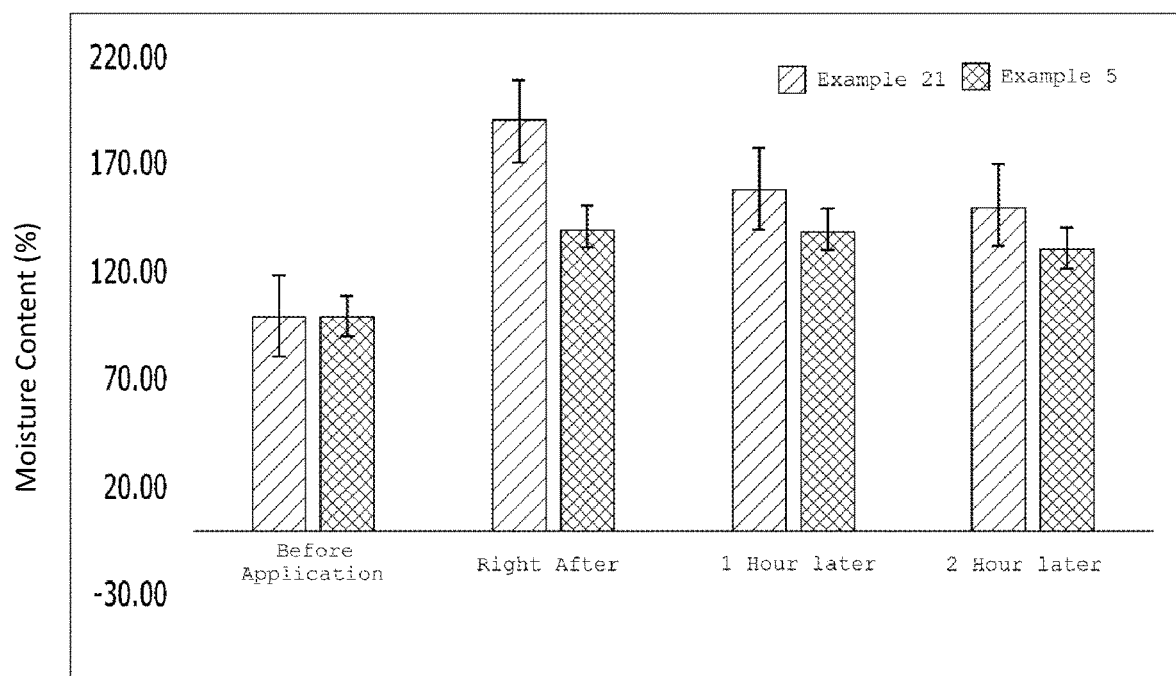
FIG. 5 shows an evaluation result of skin moisturizing degree of cream cosmetics according to Example 21 of the present invention and Comparative Example 5.

Experimental Example 4: Evaluation of Skin Moisturizing Power of Cream Cosmetic A moisturizing ability of the cream cosmetic prepared in Preparation Example 6 was evaluated as follows. After washing the forearm of a tester with water, 10 μl of cream cosmetic was applied to an area of 2 cm×2 cm and spread well using a latex glove, the moisture content in the stratum corneum was measured immediately after application, after 1 hour, and after 2 hours, respectively, by using a moisture meter of Janus Premium (Pie, Korea), which uses the principle that resistance decreases when alternating current is applied if water is contained. The results are shown in FIG. 5. As shown in FIG. 5, the cream cosmetic (Example 21) containing the mixed composition of the dead cells and the cultures of lactic acid bacteria shows a superior moisture content increase and a moisturizing ability compared to the cream cosmetic (Comparative Example 5) that does not contain the mixed composition of the dead cells and the cultures of lactic acid bacteria.

What is claimed is:

1. A cosmetic composition for preventing or improving skin aging that prevents or improves skin aging through antioxidation, anti-inflammation, moisturizing enhancement, wrinkle improvement and skin tone lightening, comprising:
   a culture of one or more lactic acid bacteria selected from a group consisting of *Lactobacillus plantarum* Wikim 125 deposited under Accession No. KCCM13498P, *Lactobacillus plantarum* Wikim 126 deposited under Accession No. KCCM13499P, and *Lactobacillus plantarum* Wikim 127 deposited under Accession No. KCCM13500P.

2. The cosmetic composition of claim 1, further comprising dead cells of one or more lactic acid bacteria selected from a group consisting of *Lactobacillus plantarum* Wikim 125 deposited under Accession No. KCCM13498P, *Lactobacillus plantarum* Wikim 126 deposited under Accession No. KCCM13499P, and *Lactobacillus plantarum* Wikim 127 deposited under Accession No. KCCM13500P.

3. The cosmetic composition of claim 1, wherein the *Lactobacillus plantarum* Wikim 125 deposited under Accession No. KCCM13498P is isolated from Kimchi.

4. The cosmetic composition of claim 1, wherein the *Lactobacillus plantarum* Wikim 126 deposited under Accession No. KCCM13499P and the *Lactobacillus plantarum* Wikim 127 deposited under Accession No. KCCM13500P are isolated from Sauerkraut prepared from cabbage or brussels sprout.

5. The cosmetic composition of claim 1, wherein the culture of the one or more lactic acid bacteria is formed by lyophilizing supernatant obtained by culturing the lactic acid bacteria in a lactic acid bacteria culture medium and performing centrifugation.

6. The cosmetic composition of claim 2, wherein the dead cells of the one or more lactic acid bacteria are obtained by culturing the lactic acid bacteria in a lactic acid bacteria culture medium, performing centrifugation, and then heat-treating precipitated cells of the lactic acid bacteria.

7. The cosmetic composition of claim 2, wherein the *Lactobacillus plantarum* Wikim 125 deposited under Accession No. KCCM13498P is isolated from Kimchi.

8. The cosmetic composition of claim 2, wherein the *Lactobacillus plantarum* Wikim 126 deposited under Accession No. KCCM13499P and the *Lactobacillus plantarum* Wikim 127 deposited under Accession No. KCCM13500P are isolated from Sauerkraut prepared from cabbage or brussels sprout.

* * * * *